US005583114A

United States Patent [19]
Barrows et al.

[11] Patent Number: 5,583,114
[45] Date of Patent: Dec. 10, 1996

[54] ADHESIVE SEALANT COMPOSITION

[75] Inventors: Thomas H. Barrows, Cottage Grove; Terry W. Lewis, Woodbury; Myhanh T. Truong, Blaine, all of Minn.

[73] Assignee: Minnesota Mining and Manufacturing Company, Saint Paul, Minn.

[21] Appl. No.: 281,473

[22] Filed: Jul. 27, 1994

[51] Int. Cl.$^6$ .......................... A61K 38/00; A61K 39/00; C07K 1/00

[52] U.S. Cl. ..................................... 514/21; 514/2; 514/4; 530/362; 530/363; 530/366; 530/830; 424/77; 424/78.02; 424/78.06; 424/179.1; 424/193.1; 424/194.1; 424/422; 424/423; 424/428; 525/54.1

[58] Field of Search ..................... 514/21, 2, 4; 530/350, 530/362, 363, 366, 830; 424/77, 78.02, 78.06, 422, 423, 428; 524/54.1

[56] References Cited

U.S. PATENT DOCUMENTS

| | | | |
|---|---|---|---|
| 2,688,610 | 9/1954 | Elins et al. | 260/117 |
| 4,101,380 | 7/1978 | Rubinstein et al. | 530/350 |
| 4,163,097 | 7/1979 | Baumann et al. | 525/531 |
| 4,356,819 | 11/1982 | Potaczek | 128/156 |
| 4,416,814 | 11/1983 | Battista | 260/117 |
| 4,670,417 | 6/1987 | Iwasaki et al. | 514/6 |
| 4,692,462 | 9/1987 | Banerjee | 514/449 |
| 4,839,345 | 6/1989 | Doi et al. | 514/21 |
| 4,851,513 | 7/1989 | Devore et al. | 530/356 |
| 5,162,430 | 11/1992 | Rhee et al. | 525/54.1 |
| 5,385,606 | 1/1995 | Kowanko | 106/124 |

FOREIGN PATENT DOCUMENTS

| | | |
|---|---|---|
| 0194807A3 | 9/1988 | European Pat. Off. |
| 2551660 | 3/1985 | France |
| WO90/13540 | 11/1990 | WIPO |
| WO92/02238 | 2/1992 | WIPO |
| WO94/03155 | 2/1994 | WIPO |

OTHER PUBLICATIONS

Abuchowshi et al, *The Journal of Biological Chemistry*, vol. 252, No. 11, pp. 3578–3581, Jun. 10, 1977.

D'Urso et al, *Biotechnology Techniques*, vol. 8, No. 2, pp. 71–76, Feb. 1994.

Two-Component Fibrin Sealant Tisseel® Kit Brochure.

Abstract, Abdella et al., "A New Cleavable Reagent for Cross-linking and Reversible Immobilization of Proteins", *Biochem. Methods*, 91:16228v, 1979.

Kalman et al., "Synthesis of a Gene for Human Serum Albumin and Its Expression in *Sacchromyces cerevisiae*", *Nucleic Acids Research*, vol. 18, No. 20, 1990, pp. 6075–6081.

Sleep et al., "The Secretion of Human Serum Albumin from the Yeast *Saccharomyces cerevisiae* Using Five Different Leader Sequences", *Bio/Technology*, vol. 8, Jan. 1990, pp. 42–46.

Sijmons et al., "Production of Correctly Processed Human Serum Albumin in Transgenic Plants", *Bio/Technology*, vol. 8, Mar. 1990, pp. 217–221.

Quirk et al., "Production of Recombinant Human Serum Albumin from *Saccharomyces cerevisiae*", *Biotechnology and Applied Biochemistry*, 11,273-287 (1989).

D'Urso et al., "New Hydrogel Based on Polyethylene Glycol Cross-Linked with Bovine Serum Albumin", *Biotechnology Techniques*, vol. 8, No. 2 (Feb. 1994) pp. 71–76.

*Primary Examiner*—Elizabeth C. Weimar
*Assistant Examiner*—Abdel A. Mohamed
*Attorney, Agent, or Firm*—Gary L. Griswold; Walter N. Kirn; Paul W. Busse

[57] ABSTRACT

This invention is related to an adhesive composition which may be used to bond or seal tissue in vivo. The adhesive composition is readily formed from a two component mixture which includes a first part of a protein, preferably a serum albumin protein, in an aqueous buffer having a pH in the range of about 8.0–11.0 and a second part of a water-compatible or water-soluble bifunctional crosslinking agent. When the two parts of the mixture are combined, the mixture is initially a liquid which cures in vivo on the surface of tissue in less than about one minute to give a strong, flexible, pliant substantive composition which bonds to the tissue and is absorbed in about four to sixty days. The adhesive composition may be used either to bond tissue, to seal tissue or to prevent tissue adhesions caused by surgery.

17 Claims, 3 Drawing Sheets

Fig. 1

Fig.3

ADHESIVE SEALANT COMPOSITION

The present invention is generally related to an adhesive sealant composition which may be used to bond or seal tissue in vivo and is particularly related to a two component, liquid adhesive composition which is mixed together as it is applied to tissue and then cured in vivo in order to bond tissue, to seal tissue to prevent or control pulmonary system air leaks, or to prevent tissue adhesions caused by surgery.

BACKGROUND

A variety of techniques have been used to bond or seal tissue. For example, different types of tissues have been mechanically bound or sealed with a number of procedures, materials and methods including sutures, staples, tapes and bandages. In some applications, these materials are made of absorbable materials which are intended to bond and/or seal tissue as it heals and then to be absorbed over a period of time.

The common use of a medical adhesive or "tissue glue" has not found widespread application. To date, some adhesive materials are known which may be used to adhere or stick tissue such as skin. For example, cyanoacrylate adhesives such as HISTOACRYL adhesive available from B. Braun, Melsungen, Germany or VETBOND tissue adhesive available from 3M, St. Paul, Minn. may be used to bond tissue. In addition to cyanoacrylate adhesives, other types of materials have been reported to adhere or stick to skin. For example, U.S. Pat. No. 4,839,345 to Doi et al. reports a hydrated crosslinked protein adhesive gel that is used as a cataplasm or cosmetic mask that will externally adhere to skin but can be easily removed or pulled off and then readhered to the skin. Other crosslinked protein hydrogels have been reported to serve as a proteinaceous substrate to deliver therapeutic agents such as enzymes or drugs through skin or mucous membranes. See, for example, International Patent Application Ser. No. PCT/US93/07314 filed Aug. 4, 1993. Still other materials have been used as hemostatic agents to stop or prevent bleeding. In particular, mixtures of fibrinogen and thrombin such as TISSEEL sealant available from Immuno AG, Vienna, Austria or BERIPLAST-P hemostatic agent or sealant available from Behringwerke, Marburg, Germany, have been used in vascular surgery to seal tissue such as blood vessels and thus prevent blood leakage.

In sum, there are few available adhesive compositions that have sufficient strength, biocompatibility and bioabsorbability as well as other desired properties that would allow such compositions to be readily used in current medical procedures or practices. The unavailability of a suitable tissue adhesive or sealant may be related to the stringent requirements that a suitable, useful tissue adhesive must meet. Importantly, a tissue adhesive must provide substantial bonding strength for either internal or external tissues. The adhesive should be made of a biocompatible material which does not interfere with normal healing or regeneration processes. A suitable tissue adhesive must also be easily administered in a liquid form and then rapidly cured, ideally in less than a minute, once applied. In addition, a tissue adhesive must remain flexible, pliant and have good mechanical strength after being cured. Finally, a tissue adhesive must be completely absorbed or broken down in vivo, without producing an allergic response, adverse tissue reaction or systemic toxic effects, in an acceptable time period. Preferably a suitable adhesive would also be readily absorbed after it is applied.

SUMMARY OF THE INVENTION

The present invention is a nontoxic, absorbable adhesive sealant composition which may be used to bond and/or seal tissue. The adhesive composition is readily formed from a two component mixture which includes a first part of a protein, preferably a serum protein such as albumin, in an aqueous buffer having a pH in the range of about 8.0–11.0 and a second part of a water-compatible or water-soluble bifunctional crosslinking agent. When the two parts of the mixture are combined, the mixture is initially liquid. The combined mixture then cures in vivo on the surface of tissue in less than about one minute to give a strong, flexible, pliant substantive composition which securely bonds to the tissue and is readily absorbed in about four to sixty days, preferably in about four to twenty-eight days.

In a preferred embodiment of the invention, an adhesive sealant composition is formed from a two part mixture that includes a proportion of a volume of a buffered basic serum albumin protein solution to a volume of a polyethylene glycol disuccinimidoyl succinate crosslinking agent in a range of from about 1:10 parts albumin solution by volume to about 10:1 parts by volume crosslinking agent. In order to facilitate the mixing of the two parts of the present adhesive composition, the volume to volume ratio of albumin solution to crosslinking agent is preferably a ratio of 1:1.

Preferred serum albumin proteins are selected to prevent adverse tissue or unwanted immunological responses. When the present adhesive mixture is used to bond or seal human tissue, a preferred serum albumin is purified human serum albumin which has been sterilized, dialyzed with a basic buffer having a pH value of about 8.0–11.0, concentrated by ultrafiltration through a membrane having about a 50,000 molecular weight cut-off to yield a concentrated, buffered aqueous mixture having about 20–60 wt/vol %, preferably about 35–45 wt/vol %, human serum albumin.

Preferred bifunctional crosslinking agents include polyethylene glycol derived crosslinking agents having a molecular weight (weight average) in a range of about 1,000–15,000 and preferably in a range of about 2,006–4,000. When the molecular weight of the crosslinking agent is in the range of about 1,000–5,000 the crosslinking agent is generally dissolved in water at a concentration of about 50–300 mg/ml. Similarly, when the molecular weight of the crosslinking agent is in the range of about 5,000–15,000 the crosslinking agent is generally dissolved in water at a concentration in the range of about 300–800 mg/ml.

The adhesive composition of this invention may be used in a variety of applications. Some applications include using the adhesive sealant composition to bind tissue together either as an adjunct to or as a replacement of sutures, staples, tapes and/or bandages. In another application, the present adhesive may be used to prevent post-surgical adhesions. In this application, the adhesive composition is applied and cured as a layer on surfaces of internal organs or tissues in order to prevent the formation of adhesions at a surgical site as the site heals. Additional applications include sealing tissues to prevent or control blood or other fluid leaks at suture or staple lines as well as to prevent or control air leaks in the pulmonary system.

DETAILED DESCRIPTION

The present invention is related to an adhesive composition which has high mechanical strength, flexibility, fast cure rate and sufficient adhesion needed to bond and/or seal tissue in vivo. The adhesive composition is made of two components, a buffered basic protein solution and a bifunctional crosslinking agent. The buffered protein solution and the bifunctional crosslinking agent are typically prepared using commercially available materials and established synthetic methods. The use of known, commercially available materials in the preparation of the adhesive composition provides a benefit in the practice of this invention because most of these materials generally have a history of clinical safety and/or use.

Suitable proteins for use in the present adhesive composition include nonimmunogenic, water soluble proteins. Serum lipoproteins are particularly well suited for this purpose because these proteins bind to lipids and also exhibit a relatively high elasticity in the natured or semi-natured state. These properties are believed to provide a cured matrix which is strong as well as pliant and elastic. Other soluble proteins, in addition to serum lipoproteins, are also suitable for use in the present invention. Aqueous mixtures of proteins such as derivatives of elastin, fibrinogen and collagen may be used in the present invention.

Preferred buffered protein solutions which may be used in the present adhesive composition include concentrated aqueous serum albumin protein mixtures that are buffered to a pH of between about 8.0–11.0 where the buffer concentration is in a range of about 0.01–0.25 molar. Suitable buffer systems include buffers which are physiologically and/or clinically acceptable such as known carbonate or phosphate buffer systems, provided the buffer does not adversely react with or otherwise alter the crosslinking agent. A preferred buffer system is a carbonate/bicarbonate buffer system at a pH value of about 9.0–10.5 at a concentration in the range of 0.05–0.15 molar.

Serum albumin protein is readily isolated from serum using known isolation processes. In addition, it is possible to produce human serum albumin from genetically transformed cells. See, for example, the reports of Quirk et al., *Biotechnology and Applied Biochemistry*, 11:273–287 (1989), Kalman et al., *Nucleic Acids Research*, 18:6075–6081 (1990), Sleep et al., *Biotechnology*, 8:42–46 (1990), and Sijmons et al., *Biotechnology*, 8:217–221 (1990). The ability to produce human serum albumin recombinantly provides the benefit that protein produced by this method will be free of pathogens, viruses or other contaminants that might contaminate albumin that is isolated directly from serum.

When used in the present buffered mixtures it has been found that the serum albumin is not denatured. Because the albumin is not denatured before it is used it is believed that the albumin proteins retain their natured, coiled conformation and thus, after being crosslinked during the curing process to provide a gel-like solid, the cured adhesive retains sufficient flexibility to provide a suitable adhesive matrix.

A variety of suitable crosslinking agents may be used in the present invention. Preferred crosslinking agents include a polyethylene glycol or polyoxyethylene chain portion (—PEG—), an activated leaving group portion (—G) and a linking moiety (—LM—) which binds the —PEG— portion and the leaving group portion —G. Crosslinking agents include compounds of the formula in which —PEG— is a diradical fragment represented by the formula where a is an integer from 20–300; —LM— is also a diradical fragment such as a carbonate diradical represented by the formula, —C(O)—, a monoester diradical represented by the formula, —(CH$_2$)$_b$C(O)— where b is an integer from 1–5, a diester diradical represented by the formula, —C(O)—(CH$_2$)$_c$—C(O)— where c is an integer from 2–10 and where the aliphatic portion of the radical may be saturated or unsaturated, a dicarbonate represented by the formula —C(O)—O—(CH$_2$)$_d$—O—C(O)— where d is an integer from 2–10, or an oligomeric diradical represented by the formulas —R—C(O)—, —R—C(O)—(CH$_2$)$_c$—C(O)—, or —R—C(O)—O—(CH$_2$)$_d$—O—C(O)— where c is an integer from 2–10, d is an integer from 2–10, and R is a polymer or copolymer having 1–10 monomeric lactide, glycolide, trimethylene carbonate, caprolactone or p-dioxanone fragments; and —G is a leaving group such as a succinimidyl, maleimidyl, phthalimidyl, or alternatively, nitrophenyl, imidazolyl or tresyl leaving groups.

The —PEG— portion of the crosslinking agent is preferably derived from commercially available compounds having a weight average molecular weight in the range of about 1,000–15,000, preferably having a weight average molecular weight in the range of about 2,000–4,000. These compounds have been used in different types of biomedical materials because they have been demonstrated to be non-toxic as well as rapidly excreted from the body when the molecular weight is below about 30,000.

The leaving group, —G, portion of the crosslinking agent is an activated leaving group which allows the crosslinking agent to react or chemically bind to free primary or secondary amine groups of a protein. Suitable leaving groups include succinimidyl, other imides such as maleimidyl and phthalimidyl, heterocyclic leaving groups such as imidazolyl, aromatic leaving groups such as a nitrophenyl, or fluorinated alkylsulfone leaving groups such as tresyl (CF$_3$—CH$_2$—SO$_2$—O—). A preferred leaving group is the succinimidyl group because studies of the mutagenicity, oncogenicity and teratogenicity of this group suggest that the small amount of this activating group which is released as the crosslinking reaction and/or the adhesive composition cures does not present a local or systemic toxicology risk.

When used in the present composition the linking moiety, —LM—, may be several different types of divalent compounds. For example, commercially available compounds having the —PEG— portion and the —G portion linked with a saturated dicarboxylic acid such as succinic acid to give a saturated diester linking moiety. Alternatively, an unsaturated dicarboxylic acid such as fumaric, maleic, phthalic or terephthalic acid may be used to give an unsaturated diester linking moiety. Alternatively, the linking moiety may be a readily hydrolyzable compounds such as oligomer derivatives of polylactic acid, polyglycolic acid, polydioxanone, polytrimethylene carbonate, or polycaprolactone as well as copolymers made using suitable monomers of these listed polymers.

In another embodiment of this invention an activated leaving group may be attached directly to a carbonate ester of polyethylene glycol. In this embodiment the linking moiety, —LM—, would be a carbonate group, —C(O)— between the —PEG— and —G portions of the crosslinking agent. In still other embodiments of this invention the linking moiety may be a dicarbonate such as ethylene carbonate which is prepared by linking the —PEG and —G portions with ethylene bischloroformate.

The crosslinking agents may be prepared using known processes, procedures or synthetic methods such as the procedures reported in U.S. Pat. Nos. 4,101,380 or 4,839,345, the procedure reported in International Application Ser. No. PCT/US90/02133 filed Apr. 19, 1990 or the procedure reported by Abuchowski et al., *Cancer Biochem. Biophys.*, 7:175–186 (1984). Briefly, polyethylene glycol and a suitable acid anhydride are dissolved in a suitable polar organic solvent in the presence of base and refluxed for a period of time sufficient to form a polyethylene glycol diester diacid. The diester diacid is then reacted with a leaving group such as an N-hydroxy imide compound in a suitable polar organic solvent in the presence of dicyclohexylcarbodiimide or other condensing agents and stirred at room temperature to form the desired bifunctional crosslinking agent.

Alternatively, polyethylene glycol and a suitable dicarboxylic acid chloride or bischloroformate may be dissolved in a suitable polar organic solvent for a period of time sufficient to form the mixed acid chloride polyethylene glycol ester or mixed chloroformate polyethylene glycol ester. The mixed esters may then be reacted with a compound such as an N-hydroxy imide compound in a suitable polar organic solvent and stirred at an elevated temperature for a period of time sufficient to form the desired bifunctional crosslinking agent.

It has also been found that the cure time of the present adhesive compositions may be tailored by use of buffers having different pH values. For example, by varying the pH of the buffer it is possible to change the cure rate time from about 10 seconds to less than about 10 minutes. Briefly, mixing concentrated aqueous serum albumin and crosslinking agent mixtures with higher concentrations of buffer provides the fastest cure times. It has also been found that higher concentrations of protein and crosslinking agent provide a relatively stronger, cured matrix. However, if the mixtures are too concentrated and viscosity becomes too great, these adhesive compositions are not as readily applied or may provide adhesives with undesired properties. For example, mixtures which are too viscous may not be readily applied using available applicators such as syringes or spray apparatus. In addition, if the concentration of crosslinking agent is too high, the resulting cured adhesive matrix may swell to such an extent that the strength of the matrix in the presence of water or other fluids is lowered. Further, ability to adequately mix the two components using injecting and/or spraying apparatus may be reduced.

The two component adhesive composition of the present invention may be applied to tissue in a number of different ways. For example, the adhesive may be quickly mixed together and then applied using common applicators. Alternatively the two components may be mixed together and then applied as spray. In another application method, the two parts of the adhesive are added to a dual syringe. The two barrels of the syringe are attached to a "Y" connect which is fitted to a spiral mixer nozzle. As the two components are pressed out of the syringe, they are mixed in the nozzle and may be directly applied to the tissue as needed in a relatively uniform, controlled manner. Alternatively, a spray nozzle tip, such as a TISSEEL spray tip sold by Immuno AG, Vienna, Austria for use with a two-component fibrin sealant kit, may be used in place of the spiral mixer nozzle. In this application, a fine spray of the adhesive composition is deposited on tissue as the plungers of the syringe are depressed.

The adhesive composition of the present invention may be used in a variety of current medical procedures and practices. In one application, the present adhesive composition may be used to eliminate or substantially reduce the number of sutures normally required using current practices as well as eliminate the need for subsequent removal of certain sutures. In another application, this adhesive composition may be used to attach skin grafts and to position tissue flaps or free flaps during reconstructive surgery. In still another application, this adhesive composition may be used to close gingival flaps in periodontal surgery. In all of these applications, the present adhesive composition is a thin layer of cured material which is effectively sandwiched between two adjacent layers of living tissues. Due to bioabsorbability and lack of toxicity of the adhesive composition, the healing and subsequent reattachment of the two layers of tissue to each other is not hampered.

In addition to the use of the present adhesive composition as an adhesive per se, the present composition may also be used as a sealant. When used in this application, this composition may be used to prevent air leaks now associated with pulmonary surgery or to inhibit or prevent bleeding in other surgical procedures. When used in this manner, the underlying tissue may be coated with a relatively thick layer of adhesive since the tissue itself needs to only heal on one side. The other side of the of the adhesive, when cured, simply presents a lubricous gel which will be absorbed in vivo in a relatively short period of time from about four to sixty days. In view of this property of the present adhesive composition, it may also be used to prevent unwanted tissues adhesions which are associated with current surgical procedures.

EXAMPLES

The following examples are intended to describe and illustrate the practice of the claimed invention. The examples, however, should not be construed to limit the scope of the present invention which is defined by the appended claims.

The following procedures were used to prepare several different types of bifunctional crosslinking agents. The following procedures are modifications of procedures reported in U.S. Pat. No. 4,101,380 and Abuchowski et at., cited above.

Example 1

Synthesis Of Polyethylene Glycol Disuccinimidyl Succinate PEG-SS2

Polyethylene glycol, PEG, (50 g, Aldrich Chemical Company, Milwaukee, Wis., sold as 3,400 average molecular weight, GPC analysis $M_n$ was 2,980, $M_w$, was 3,480) was dissolved in 1,2-dichloroethane (250 ml) containing succinic arthydride (14.7 g) and anhydrous pyridine (12 ml). The mixture was refluxed under nitrogen for three days. After filtration and evaporation of the solvent, the residue was dissolved in 100 ml water and treated with the cation exchange resin Dowex™ 50 (H⁺) (50 g) for 30 minutes. The mixture was then filtered and the Dowex™ 50 was washed with water (50 ml 1×). The combined filtrate was washed with anhydrous diethyl ether (50 ml 2×). The PEG-disuccinate was then extracted from the water phase with two 100 ml chloroform washes. Evaporation of chloroform yielded about 49 g of PEG-disuccinate.

The PEG-disuccinate was dissolved in 200 ml N,N-dimethylformamide (DMF) at 37° C. and 4.23 g of N-hydroxysuccinimide (NHS) were added to the solution. The mixture was cooled to 0° C. 7.58 g of dicyclohexylcarbodiimide (DCC) were dissolved in 50 ml DMF and added dropwise to the above solution with continuous stirring. The mixture was left at room temperature for 24 hours and filtered. 100 ml of toluene were added to the filtrate and the solution was placed in an ice bath. The desired polyethylene glycol disuccinimidyl succinate product, PEG-SS2, was precipitated by slowly adding petroleum ether. The precipitate was collected on a 10–20 micron sintered glass filter. Dissolution in toluene and precipitation with petroleum ether was repeated three times. The PEG-SS2 was further purified by dissolving in 100 ml of 0.1M pH 2.2 citrate/phosphate buffer and filtering through a 4–8 micron sintered glass filter. The PEG-SS2 was extracted with chloroform (100 ml 2×) and the solvent was evaporated under reduced pressure in a rotary evaporator. The PEG-SS2 was then dissolved in toluene and precipitated with petroleum ether, dried under vacuum overnight at room temperature, and stored in a refrigerator.

Example 2

Synthesis of N-hydroxysuccinimide Ester of Dicarboxymethyl Polyethylene Glycol

Dicarboxymethyl poly(ethylene glycol) (mol. wt. 3400) purchased from Shearwater Polymers, Inc., Huntsville, Ala. (5 g) and N-hydroxysuccinimide purchased from Sigma Chemical Co., St. Louis, Mo. (1 g) were dissolved in 30 ml of anhydrous DMF with mechanical stirring under nitrogen. The solution was cooled to 0° C. and a solution of dicyclohexylcarbodiimide (1.79 g) in 5 ml DMF was added dropwise. The stirring was continued in the cold for 3 hours then at room temperature overnight (16 hrs). Dicyclohexylurea which precipitated was removed by filtration. Toluene (100 ml) was added to the filtrate and cooled to 0° C. The product was then precipitated by addition of petroleum ether. The precipitate was collected on a sintered glass filter. Dissolution in toluene and reprecipitation with petroleum ether was repeated three times. The product was dried under vacuum in a desiccator.

Example 3

Synthesis of Polyethylene Glycol-di-oligoglycolide Disuccinimidyl Succinate

A 500 ml three neck round bottom flask was flame dried under nitrogen. 50 g of PEG (mol. wt. 3400), 300 ml of xylene, and 1 drop of 0.33M stannous ottoate solution in xylene were charged into the flask with a continuous nitrogen purge. The flask was heated to boil the solution and 50 ml of xylene were removed by distillation. The solution was then cooled to room temperature. 17 g of glycolide (Boehfinger Ingleheim KG, Ingleheim, Germany) was added to the flask and the reaction mixture was refluxed under nitrogen for 16 hours. The copolymer reaction mixture was filtered hot to remove polyglycolide homopolymer. The copolymer then precipitated from the filtrate upon cooling and collected by filtration. The copolymer was placed in a flask with 500 ml of dichloromethane and 7 g of succinyl chloride. The solution was refluxed under nitrogen overnight (16 hours). 8.5 g of N-hydroxysuccinimide was added to the flask and refluxing was continued for another overnight period. A white solid was obtained by precipitation upon cooling the solution. The product was then purified by redissolving in toluene and reprecipitating with petroleum ether several times. The final precipitate was dried under vacuum and stored in a desiccator. The structure of the product was confirmed by NMR analysis.

Example 4

Synthesis of Polyethylene Glycol-dimaleimidyl Succinate

About 12 g of PEG-disuccinate and 1 g N-hydroxymaleimide (Aldrich Chemical Co.) were placed in a 250 ml three neck round bottom flask with 50 ml of anhydrous DMF under nitrogen. The mixture was dissolved at 60° C. with mechanical stirring and cooled to 0° C. A solution of 1.82 g dicyclohexylcarbodiimide in DMF (5 ml) was added dropwise to the flask. The reaction was allowed to mix overnight under nitrogen at room temperature. Dicyclohexylurea was removed by filtration and the product was obtained by adding toluene and precipitating with petroleum ether. Dissolution in toluene and reprecipitation with petroleum ether were repeated three times. The purified product was dried under vacuum and stored in a desiccator.

Example 5

Synthesis of Polyethylene Glycol-diphthalimidyl Succinate

About 15 g of PEG-disuccinate and 1.65 g N-hydroxyphthalimide (Aldrich Chemical Co.) were placed in a 250 ml three neck round bottom flask with 30 ml of anhydrous DMF under nitrogen. The mixture was dissolved at 60° C. with mechanical stirring and cooled to 0° C. A solution of 1.82 g dicyclohexylcarbodiimide in DMF (5 ml) was added dropwise to the flask. The reaction was allowed to mix overnight under nitrogen at room temperature. Dicyclohexylurea was removed by filtration and the product was obtained by adding toluene and precipitating with petroleum ether. Dissolution in toluene and reprecipitation with petroleum ether were repeated three times. The purified product was dried under vacuum and stored in a desiccator.

Example 6

Preparation of Two Component Adhesive

The following procedure was used to prepare a two-component adhesive using a variety of protein sources, and bifunctional crosslinking agents. Aqueous solutions of a protein and a crosslinking agent as listed in Table 1 were pipetted (0.2 ml of each solution) into a porcelain test well and mixed continuously with a stainless steel rod. The cure time and physical consistency of each of the two component adhesives are also listed in Table 1.

The data indicated that fish and bovine gelatin, egg and serum albumin as well as casein protein crosslinked with PEG-SS2 provided an adhesive which was very elastic, had good adhesive strength and a relatively rapid cure rate.

TABLE 1

| Protein | Bifunctional Crosslinking agent | Cure Time | Consistency |
|---|---|---|---|
| Fish Gelatin Lot 23H0307 Sigma 40% 0.1 M pH 10 Carb/Bicarb | 130 mg/ml PEG-SS2 3400 mw | 40 sec | Strong gel, very elastic, slightly sticky |
| Fish Gelatin Lot 23H0307 Sigma 40% 0.1 M pH 10 Carb/Bicarb | 260 mg/ml PEG-SS2 3400 mw | 40 sec | Strong gel, very elastic, slightly sticky |
| Fish Gelatin Lot 23H0307 Sigma 40% 0.1 M pH 10 Carb/Bicarb | 130 mg/ml PEG-SS2 10,000 mw | 120 sec | Soft gel, very sticky |
| Fish Gelatin Lot 23H0307 Sigma 40% 0.1 M pH 10 Carb/Bicarb | 260 mg/ml PEG-SS2 10,000 mw | 110 sec | Soft gel to elastic, moderately sticky |
| Gelatin Bovine Skin Lot 53H0271 Sigma 40% 0.1 M pH 10 Carb/Bicarb | 130 mg/ml PEG-SS2 3400 mw | 40 sec | Soft gel, not elastic |
| Gelatin Bovine Skin Lot 53H0271 Sigma 40% 0.1 M pH 10 Carb/Bicarb | 260 mg/ml PEG-SS2 3400 mw | 40 sec | Soft gel, not elastic |
| Gelatin Bovine Skin Lot 53H0271 Sigma 40% 0.1 M pH 10 Carb/Bicarb | 130 mg/ml PEG-SS2 10,000 mw | 40 sec | Soft gel, not elastic |
| Gelatin Bovine Skin Lot 53H0271 Sigma 40% 0.1 M pH 10 Carb/Bicarb | 260 mg/ml PEG-SS2 10,000 mw | 120 sec | Soft gel, not elastic |
| Casein pH 9.4 12.6% Carb/Bicarb | 130 mg/ml PEG-SS2 3400 mw | 40 sec | Strong gel, elastic, not sticky |
| Poly-L-Lysine 50 mg/ml $H_2O$ 300,000 mw Carb/Bicarb | 130 mg/ml PEG-SS2 3400 mw | 20 sec | Waxy, no adhesive strength |
| Poly-L-Lysine 50 mg/ml $H_2O$ 300,000 mw Carb/Bicarb | 260 mg/ml PEG-SS2 3400 mw | 15 sec | Waxy, no adhesive strength |
| Poly-L-Lysine 50 mg/ml $H_2O$ 300,000 mw Carb/Bicarb | 130 mg/ml PEG-SS2 10,000 mw | 10 sec | Waxy, no adhesive strength |
| Poly-L-Lysine 50 mg/ml $H_2O$ 300,000 mw Carb/Bicarb | 260 mg/ml PEG-SS2 10,000 mw | 10 sec | Waxy, no adhesive strength |
| Chicken Egg Albumin 40% 0.08 M pH 10 Carb/Bicarb | 130 mg/ml PEG-SS2 3400 mw | 210 sec | soft, tacky |
| Rabbit Serum Albumin (RSA) Sigma Lot 19F9301 40% 0.1 M pH 10 Carb/Bicarb | 130 mg/ml PEG-SS2 3400 mw | 20 sec | Very elastic, good adhesive strength, not sticky |
| Human Serum Albumin (HSA) Sigma Lot 63H9041 40% 0.1 M pH 10 Carb/Bicarb | 130 mg/ml PEG-SS2 3400 mw | 20 sec | Very elastic, good adhesive strength, not sticky |
| HSA Sigma | 130 mg/ml PEG-SS2 3400 mw | 20 sec | Very elastic, good adhesive |

TABLE 1-continued

| Protein | Bifunctional Crosslinking agent | Cure Time | Consistency |
|---|---|---|---|
| Lot 63H9041 40% 0.1 M pH 8.44 Carb/Bicarb | | | strength, not sticky |
| HSA Sigma Lot 63H9041 40% 0.1 M pH 8.44 Carb/Bicarb | 260 mg/ml PEG-SS2 3400 mw | 10 sec | Very elastic, good adhesive strength, not sticky |
| HSA Sigma Lot 63H9041 40% 0.1 M pH 8.44 Carb/Bicarb | 130 mg/ml PEG-SS2 10,000 mw | 30 sec | Very elastic, slight adhesive strength, very sticky |
| HSA Sigma Lot 63H9041 40% 0.1 M pH 8.44 Carb/Bicarb | 260 mg/ml PEG-SS2 10,000 mw | 25 sec | Very elastic, slight adhesive strength, very sticky |
| HSA Baxter Healthcare Corp. Lot 2837A238AA Carb/Bicarb | 130 mg/ml PEG-dimaleimidyl succinate Example 4 | 20 sec | Turned brown upon curing, hard gel, not sticky |
| HSA Baxter Lot 2837A238AA Carb/Bicarb | 130 mg/ml PEG-diphthalimidyl succinate Example 5 | 10 sec | Turned red upon curing, hard gel, not sticky |
| HSA Baxter Lot 2837A238AA Carb/Bicarb | 130 mg/ml PEG-dicaboxymethyl disuccinimidyl Example 2 | 8 sec | Hard gel, not sticky, no color change |
| HSA Baxter Lot 2837A238AA Carb/Bicarb | 130 mg/ml PEG-dioliglycolide disuccinimidyl succinate Example 3 | 40 sec | Hard gel, not sticky, no color change |
| HSA Baxter Lot 2837A238AA Carb/Bicarb | 130 mg/ml PEG-disuccinimidyl propionate PEG(SPA)2 | 30 sec | Hard gel, not sticky, no color change |
| HSA Baxter Lot 2837A238AA Carb/Bicarb | 260 mg/ml PEG-disuccinimidyl propionate PEG(SPA)2 | 40 sec | Hard gel, not sticky, no color change |
| HSA Baxter Lot 2837A238AA Carb/Bicarb | 130 mg/ml PEG-dioxycarbonyl imidazole PEG(CDI)2 | 48 hrs (cure) | Hard gel, not sticky, no color change |
| HSA Baxter Lot 2837A238AA Carb/Bicarb | 130 mg/ml PEG-dinitrophenyl carbonate PEG(NPC)2 | 140 sec | Hard gel, not sticky, changed to bright yellow color |
| HSA Baxter Lot 2837A238AA Carb/Bicarb | 260 mg/ml PEG-dinitrophenyl carbonate PEG(NPC)2 | 140 sec | Hard gel, not sticky, changed to bright yellow color |
| HSA Baxter Lot 2837A238AA Carb/Bicarb | 130 mg/ml PEG-ditresylate PEG(tres)2 | 8 hrs (viscous) 24 hrs (cure) | Hard gel, not sticky, no color change |
| HSA Baxter Lot 2837A238AA Carb/Bicarb | 130 mg/ml PEG-diglycidyl ether PEG(epox)2 | 72 hrs (cure) | Hard gel, not sticky, no color change |
| HSA Baxter Lot 2837A238AA Carb/Bicarb | 130 mg/ml PEG-dialdehyde PEG(ald)2 | no cure | Liquid | mw = weight average molecular weight

Example 7

Effect of Buffer and pH

Two component adhesives were prepared according to the process described in Example 6 except that the pH of the buffer in the protein solution was changed as listed in Table 2. The data indicate that a preferred pH range is about 8.44–10.0.

TABLE 2

| Protein | Crosslinking agent PEG-SS2 | Cure Time | Consistency |
| --- | --- | --- | --- |
| HSA Baxter Lot 2837A238AA 40% 0.1 M pH 7.4 Carb/Bicarb | 130 mg/ml 3400 mw | 10 min | Initially softer adhesive, hardens with aging |
| HSA Sigma Lot 63H9041 40% 0.1 M pH 8.44 Carb/Bicarb | 130 mg/ml 3400 mw | 20 sec | Very elastic, good adhesive strength, not sticky |
| HSA Sigma Lot 63H9041 40% 0.15 M pH 9.07 Carb/Bicarb | 130 mg/ml 3400 mw | 10 sec | Hard gel, not sticky |
| HSA Sigma Lot 63H9041 40% 0.2 M pH 9.52 Carb/Bicarb | 130 mg/ml 3400 mw | 5 sec | Hard gel, not sticky |
| HSA Sigma Lot 63H9041 40% 0.2 M pH 9.52 Carb/Bicarb | 260 mg/ml 3400 mw | 5 sec | Hard gel, not sticky |
| HSA Sigma Lot 63H9041 40% 0.2 M pH 9.52 Carb/Bicarb | 130 mg/ml 10,000 mw | 7 sec | Elastic to hard gel, slightly sticky |
| HSA Sigma Lot 63H9041 40% 0.2 M pH 9.52 Carb/Bicarb | 260 mg/ml 10,000 mw | 7 sec | Elastic to hard gel, slightly sticky |
| HSA Baxter Lot 2837A238AA 40% 0.1 M pH 10 Carb/Bicarb | 130 mg/ml 3400 mw | 25 sec | Very elastic, not sticky |
| HSA Sigma Lot 63H9041 40% 0.1 M pH 10 Carb/Bicarb | 130 mg/ml 3400 mw | 25 sec | Very elastic, not sticky | mw = weight average molecular weight

Example 8

Effect of Crosslinking Agent on Adhesive Strength

A 30% HSA (Human Serum Albumin) solution from Sigma Chemical Co. and a 25% HSA solution from Baxter Healthcare, Inc. were dialyzed against 0.1M carbonate/bicarbonate pH 10 buffer at 4° C. overnight and concentrated to about 40% by ultra-filtration through a 50,000 molecular weight cut-off cellulose ester disc membrane (Spectrum Medical Industries, Inc.) in a pressure filtration cell under nitrogen at 60 psig. The final concentration was calculated based on the volume of collected filtrate. The maximum concentration obtained under these conditions during overnight ultra-filtration was typically 42–45%. The RSA (Rabbit Serum Albumin) from Sigma and RSA crystallized protein from ICN Biomedical, Inc. were dissolved in 0.1M pH 10 carbonate/bicarbonate buffer and concentrated to 40% by the same method used for HSA.

Various concentrations of PEG-SS2 (3,400 mw and 10,000 mw) were prepared in deionized water. The albumins and crosslinking agent solutions were delivered in equal volume using a 1 ml dual syringe. The syringe tips were fitted with a Y connector which connected to a specially machined TEFLON adaptor inserted into a 1.8 in.×0.187 in. (4.57 cm×0.475 cm) dia. spiral mixer nozzle (TAH Industries, Inc., Robbinsville, N.J., part no. 150–312). The adhesive mixture was injected through the mixer directly onto the test substrate for adhesion testing.

Figure 1:
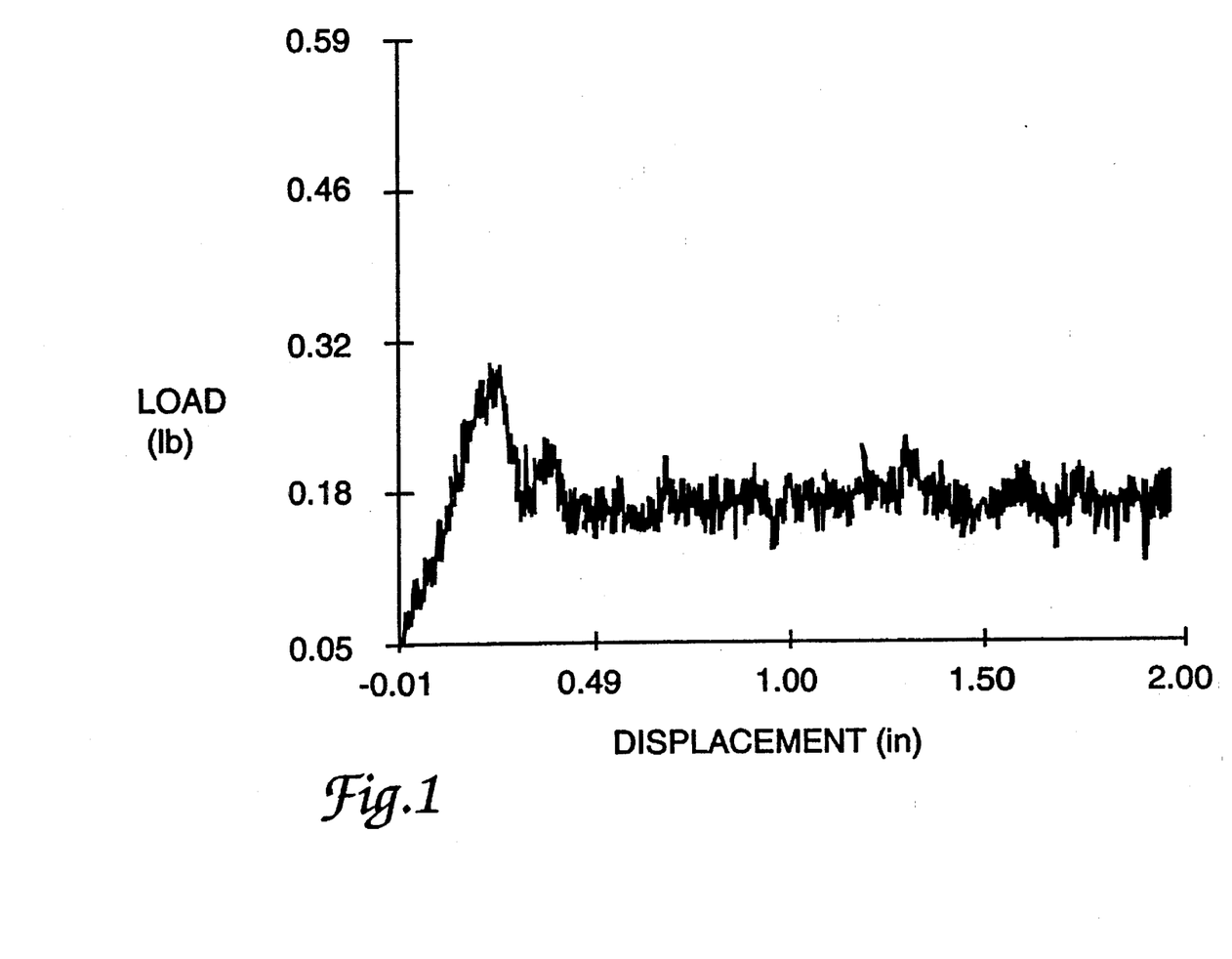
FIG. 1 is a graphical representation of a measured peel force of an adhesive composition of this invention.
Figure 2:
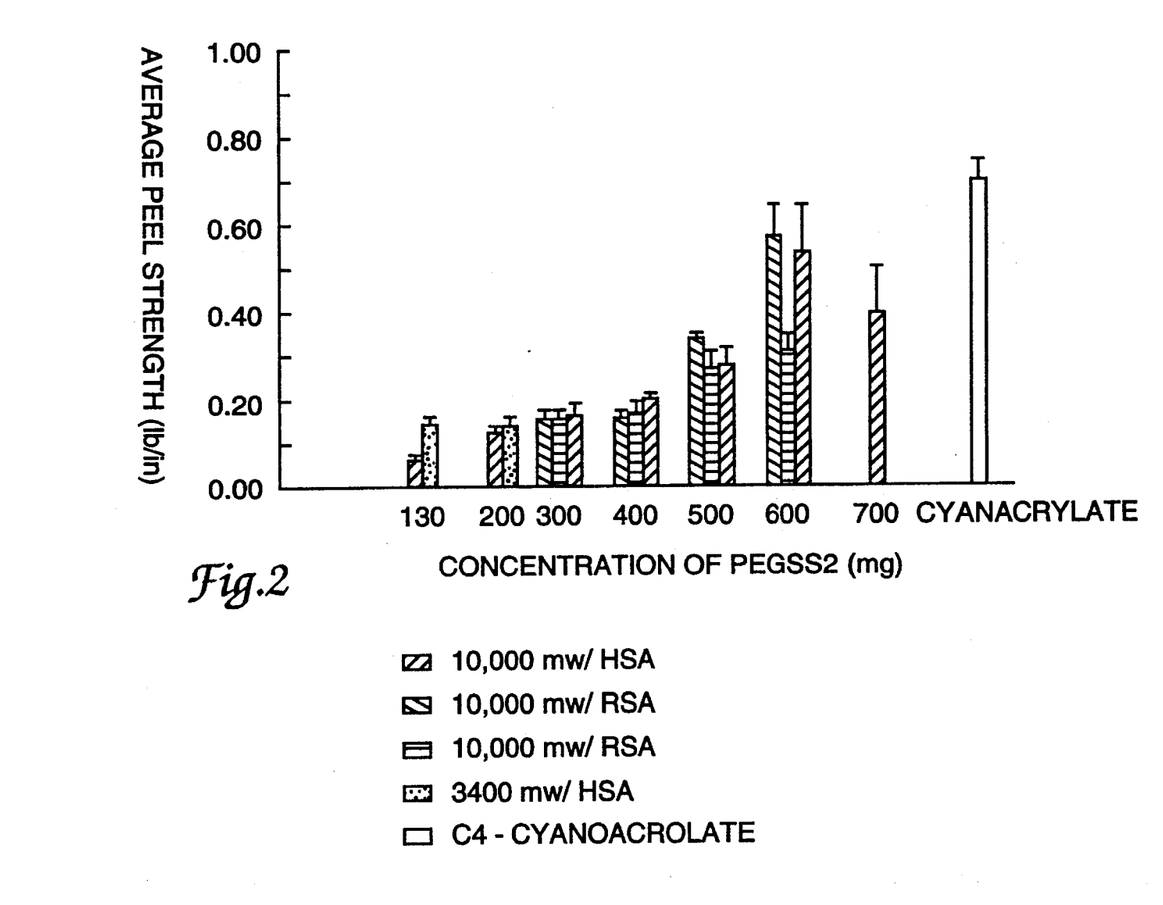
FIG. 2 is a graphical representation of peel force measurements of different adhesive composition samples which are used to adhere excised guinea pig skin strips together.

Freshly excised guinea pig skin was cut into strips and a polystyrene window with an opening of 0.5×1.0 inches (1.27 cm×2.54 cm) was placed on one end of the strip to contain the glue in a specific region. Upon filling the window with glue it was covered with another strip of guinea pig skin. A 500 g steel weight was placed on top of this assembly for about one minute. The sample was peeled apart in the jaws of a computer controlled mechanical testing machine (880 Material Test System, MTS System, Inc., Minneapolis, Minn.) set at a strain rate of 0.8 in./min. (2 cm/min.) with a gage length of 1 in. (2.54 cm) and a 5 lbs. (2.27 kg) load cell. Peel force was recorded after the initiation of adhesive failure as the constant force require to continue peeling as shown in FIG. 1. Four replicates were performed for each test condition. The results of this test are listed in FIG. 2.

Example 9

Measurement of Adhesive Sealant Burst Strength

Figure 3:
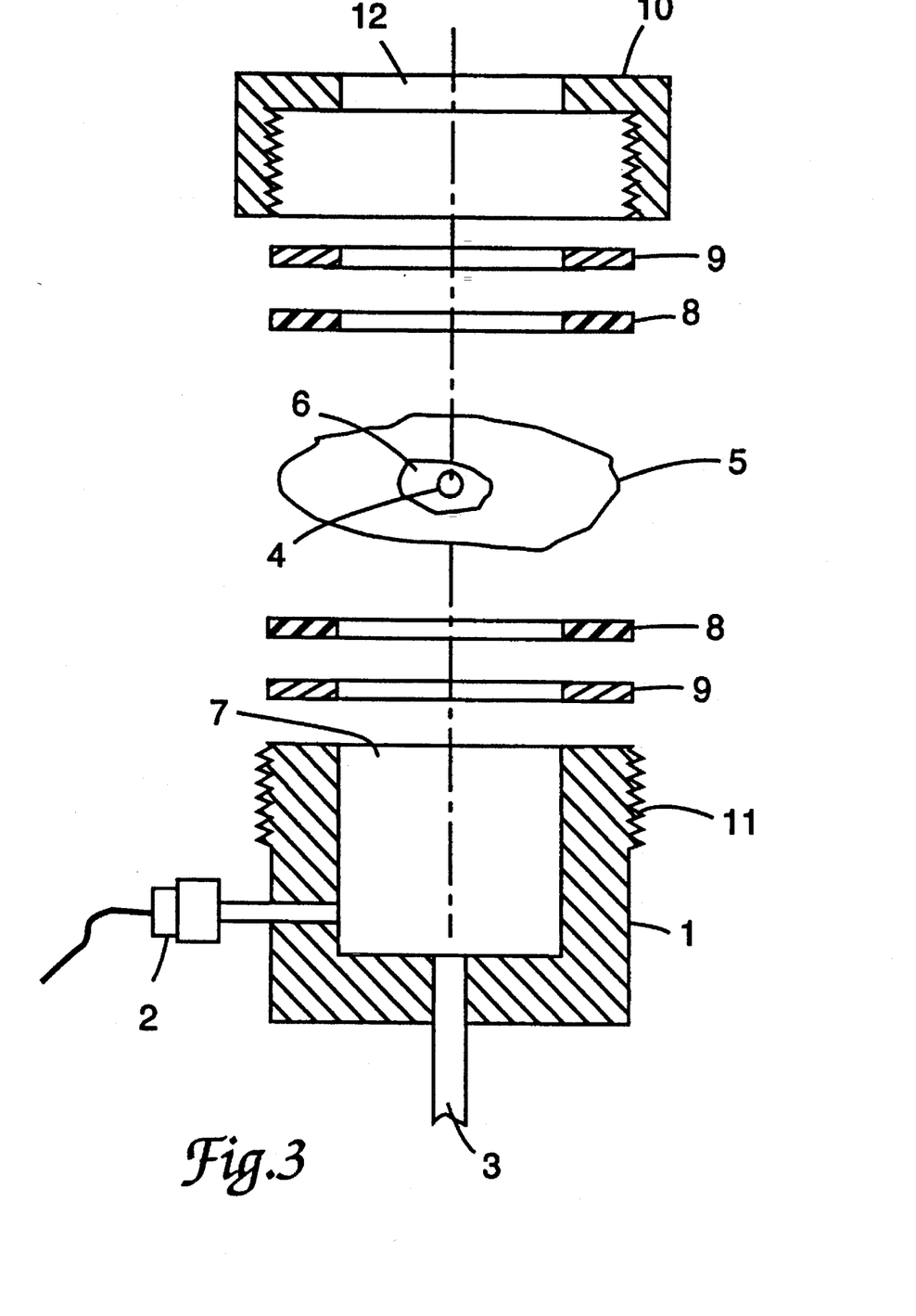
FIG. 3 is a schematic diagram of an apparatus used to measure burst strength of an adhesive sealant composition.

A pressurization assembly illustrated in FIG. 3 was used to test the bursting strength of materials used to seal standardized holes or slits in test membranes. This assembly included an aluminum pressure vessel (1) having a 35 mm inside diameter fitted with a millivolt output type pressure transducer (2) with a range of 0 to 15 psig (MODEL PX236, Omega Engineering, Inc., Stamford, Conn.) and a pressure inlet port (3). To perform a test, about a 5 mm diameter hole (4) (or other standardized defect) was cut in the center of a test membrane (5) using a die cutter. The membrane was then placed on a piece of 0.4 mm thick TEFLON film with the hole in the membrane centered in a larger (14 mm diameter) hole in the TEFLON film. The TEFLON film was then placed on a flat surface with the membrane side down and adhesive sealant test material was applied to fill the hole in the film. A solid TEFLON block was then quickly placed over the sealant prior to cure so that the TEFLON film served as a spacer to create a layer of sealant exactly 0.4 mm thick. After the desired cure time elapsed, the TEFLON block was inverted and the membrane was carefully peeled off to obtain a circular patch of sealant (6) covering the hole in the membrane. The test membrane with sealed defect was then mounted onto the open end of the pressure vessel (7) by placing it between two rubber washers (8) and then between two metal washers (9). An air tight seal was obtained by screwing the threaded cover (10) onto the matching threads (11) of the pressure vessel. The opening in the cover (12) was also 35 mm in diameter which, in combination with the 35 mm inside diameter washers, provided a fixed membrane surface area for pressure testing.

Two types of membranes were used, either a collagen membrane or a freshly excised porcine pericardium sample. The porcine pericardium sample was either used immediately upon harvest or after storage in a moisture-proof container at 4° C. for no longer than 24 hours. Under these conditions there was no discernible difference in sealant performance based on storage time of that tissue.

The pressurization sequence was initiated by injecting air into the pressure inlet at a fixed rate of one cubic centimeter per second using a syringe pump (Sage Instruments Model 351, Orion Research, Inc.). The pressure transducer was connected to a digital strain gauge meter (Omega Model DP205-S, Omega. Engineering, Inc.) programmed to read pressure (ram mercury) and to display the peak pressure value at the time of adhesive sealant rupture. Replicate tests gave reproducible peak pressure values and the standard deviation was reported in each case.

Pressure tests were performed with an adhesive composition of 40% HSA (or RSA) in 0.08M carbonate/bicarbonate buffer at different pH values with 3,400 m.wt. PEG-SS2 (130 mg/ml) on collagen and pericardium membranes. The results listed in Table 3 demonstrate excellent sealant performance with typical peak pressure values of about 130 mm Hg.

In addition, the peak pressure for the above sealants after soaking in saline solution was measured. The test was performed as described above except that the surface of the sealant coated membrane was flooded with saline for up to a time period of 90 minutes before pressurization. Although the sealant hydrogel swelled to about double in thickness, substantial retention of sealant performance was retained.

Table 4 shows the data obtained by testing a variety of proteins including fish skin gelatin, chicken egg albumin, and fibrinogen. Fibrinogen mixed with thrombin ("fibrin glue", BERIPLAST-P sealant, Behringwerke, Marburg, Germany) was also used as a control sealant material. None of these materials performed as well as the serum albumin examples. The main disadvantage was the cure and aging time required to achieve significant strength. In particular, chicken egg albumin required twenty-five minutes of post cure aging to achieve the same burst strength obtained from serum albumin aged for less than five minutes.

The same process was repeated for additional 25% HSA solutions by dialyzing against 0.08M carbonate/bicarbonate buffers at pH 9 and pH 8. A pH 7 solution of HSA was obtained by concentration of the original 25% HSA solution to 40% by ultrafiltration. The crosslinking agent solution PEG-SS2 (3400 mw) was 130 mg dissolved in one ml deionized water. The albumin and crosslinking agent solutions were delivered in equal volume using a one ml dual syringe as in Example 8. The pressure tests were performed as above using collagen membrane except that the sealant hydrogel was aged before testing. The results are also listed in Table 4. These data demonstrate that optimal pressure test values are achieved faster with increasing pH of the albumin solution. Moreover, the resultant cured sealant obtained after complete curing has taken place is unexpectedly higher with higher pH of the albumin solution.

TABLE 3

| Tissue | Tissue Opening | Adhesive Composition | Burst Pressure (mm Hg) |
|---|---|---|---|
| Collagen | 4.56 mm dia. hole | HSA:PEG-SS2 | 150 |
| Collagen | 5 mm slit | HSA:PEG-SS2 | 112 |
| Collagen | 4.56 mm dia. hole | RSA:PEG-SS2 | 130 |
| Collagen | 5 mm slit | RSA:PEG-SS2 | 125 |
| Porcine Pericardium | 4.56 mm dia. hole | HSA:PEG-SS2 | 155 |
| Porcine Pericardium | 5 mm slit | HSA:PEG-SS2 | 130 |
| Porcine Pericardium | 4.56 mm dia. hole | RSA:PEG-SS2 | 125 |
| Porcine Pericardium | 5 mm slit | RSA:PEG-SS2 | 130 |

TABLE 4

Pressure Test of Different Proteins Using Collagen and Pericardium
HSA: 40% 0.08 M Carb/Bicarb Buffer in Saline Lot #2837a328AA
RSA: 40% 0.08 M Carb/Bicarb Buffer in Saline Lot #82-451-0050 INC
PEG-SS2: 3400 mw lot #103128-110 (130 mg/ml)
Defect: 4.56 mm hole
Air Flow Rate: 1 cc/s

| Protein | Crosslinker | Membrane | Pressure (mm Hg) Ave | Stdev | Comments |
|---|---|---|---|---|---|
| HSA pH 10 | PEG-SS2 | Collagen | 149 | 9 | No bubbles |
|  |  | Pericardium | 154 | 4 | 5 min after curing |
|  |  | Pericardium | 196 | 5 | 10 min after curing |
| HSA pH 10 | PEG-SS2 | Collagen | 144 |  | 5 min after curing |
|  |  |  | 155 |  | 10 min after curing |
|  |  |  | 162 |  | 20 min after curing |
| HSA pH 9 | PEG-SS2 | Collagen | 108 |  | 5 min after curing |
|  |  |  | 114 |  | 10 min after curing |
|  |  |  | 116 |  | 20 min after curing |
| HSA pH 8 | PEG-SS2 | Collagen | 36 |  | 5 min after curing |
|  |  |  | 78 |  | 10 min after curing |
|  |  |  | 90 |  | 20 min after curing |
| HSA pH 7 | PEG-SS2 | Collagen | 30 |  | 10 min after curing |
|  |  |  | 52 |  | 20 min after curing |
| RSA pH 10 | PEG-SS2 | Collagen | 134 | 5 | No bubbles |
|  |  | Pericardium | 126 | 10 | 5 min after curing |
|  |  | Pericardium | 194 | 9 | 10 min after curing |
| Fish Gelatin pH 10 40% (Sigma) | PEG-SS2 | Collagen | 34 | 2 | 10 min after curing |

TABLE 4-continued

Pressure Test of Different Proteins Using Collagen and Pericardium
HSA: 40% 0.08 M Carb/Bicarb Buffer in Saline Lot #2837a328AA
RSA: 40% 0.08 M Carb/Bicarb Buffer in Saline Lot #82-451-0050 INC
PEG-SS2: 3400 mw lot #103128-110 (130 mg/ml)
Defect: 4.56 mm hole
Air Flow Rate: 1 cc/s

| Protein | Crosslinker | Membrane | Pressure (mm Hg) Ave | Stdev | Comments |
|---|---|---|---|---|---|
| Chicken Egg Albumin pH 10 40% (Sigma) | PEG-SS2 | Collagen | 14 151 | 3 5 | 10 min after curing 45 min after curing |
| Fibrin Glue (BERIPLAST-P) Used according to mfg. instructions | | Pericardium | 8 39 | 2 2 | 5 min after curing with saline, glue slid off easily 5 min after curing without saline, leaked underneath |
| Bovine Fibrinogen pH 10 15% (Sigma) | PEG-SS2 | Collagen | 8 8 | 2 2 | 5 min after curing 60 min after curing, glue slid off easily |

Example 10

Use of a Two Component Adhesive Sealant in General and Thoracic Surgery

An anesthetized pig was used as an experimental model for thoracic surgical complications such as staple line leaks during lung and bronchus resections, bronchopleural fistulas, and other conditions resulting in pneumothorax.

The two component adhesive included Part A, a 40% HSA prepared by dialysis of commercially available HSA (25% Solution, BUMINATE 25%, Baxter Healthcare Corp., Hyland Division, Glendale, Calif.) against 0.08M pH 10 carbonate/bicarbonate buffer followed by concentration to 40% by ultrafiltration at 50 psi using a 50,000 molecular weight cut-off cellulose ester disc membrane and Part B, a 130 mg/ml solution of 3,400 m.wt. PEG-SS2 dissolved in sterile distilled water no more than 30 minutes prior to use. The PEG-SS2 was synthesized and purified as described in Example 1.

A stab wound was made on the lung of an anesthetized pig with a scalpel which resulted in significant air leakage during inspiration as evidenced by bubbling of air through irrigation fluid administered to the site. The wound was blotted with gauze to remove blood and fluid. The respirator was turned off and the adhesive was applied as a sealant using a dual syringe (Behring PANTAJECT syringe, Behringwerke, Marburg, Germany) equipped with a spiral mixing tip. After a 20 second cure time ventilation was restored and the lung was again covered with irrigation fluid. No air leaks were observed.

A functional end-to-end anastomosis in pig intestine was conducted using a standard stapling procedure. The adhesive material described above was applied to the staple lines. This resulted in a clear, adherent hydrogel coating which appeared to seal the anastomotic line.

Under these conditions it was observed that anastomotic lines coated with the sealant were air tight whereas anastomotic lines not sealed were not air tight.

Example 11

Use of Two Component Adhesive to Prevent Post-Surgical Adhesions

The tissue sealant hydrogel tested was a two part liquid system. Part A was a sterile 40% (w/v) solution of human serum albumin in isotonic pH 10 carbonate buffer (0.1M). Part B was a 400 mg/ml solution of 10,000 molecular weight PEG-SS2 (polyethylene glycol disuccinimidyl succinate) in sterile distilled water prepared just prior to use. Solutions A and B were mixed in equal volumes with a dual syringe system connected to a static mixing head (Tah Industries, Inc.).

Post-surgical adhesion prevention evaluation of this sealant formulation was initiated in a series of ten female rabbits. A 2×2 cm area of the abdominal wall was excised down to the fascia on each side of the abdominal cavity exposed by a midline laparotomy incision. The uterine horns were injured by scraping 20 times with a no. 10 scalpel blade. Each animal served as its own control by randomly applying test material to only one of the abdominal wall injuries. The uterine horns were then attached with two stitches to the abdominal wall within a few millimeters of the edge of the wound closest to the laparotomy incision.

Two weeks after surgery the rabbits were examined in order to evaluate and score the extent, type, and tenacity of adhesions present on the abdominal wall injury sites. These results are shown in Table 5. The rating system used to obtain these scores is shown in Table 6. Although technical difficulties were encountered as noted in Table 5, the test material clearly provided an unexpected benefit in both the prevention of adhesions and a reduction in their severity without the presence of a known active ingredient.

TABLE 5

Scoring of Adhesions Formed in Material Evaluation

| Animal | Extent Control | Extent Treatment | Type Control | Type Treatment | Tenacity Control | Tenacity Treatment |
|---|---|---|---|---|---|---|
| BAM 8 | 2 | 0+ | 3 | 0+ | 3 | 0+ |
| BAM 9 | 3 | 1 | 3 | 1 | 3 | 1 |
| BAM 10 | 0+ | 1 | 0+ | 3 | 0+ | 2 |
| BAM 11 | 0* | 0 | 0* | 0 | 0* | 0 |
| BAM 12 | 4 | 4 | 3 | 3 | 3 | 3 |
| BAM 13 | 2 | 1 | 3 | 2 | 3 | 2 |
| BAM 14 | 1* | 0 | 3* | 0 | 3* | 0 |
| BAM 15 | 1 | 0** | 1 | 0** | 2 | 0** |
| BAM 16 | 1 | 0* | 1 | 0* | 2 | 0* |
| BAM 17 | 1 | 0* | 1 | 0* | 2 | 0* |
| Average | 1.5 | 0.7 | 1.8 | 0.9 | 2.1 | 0.8 |

*Uterine horn tacked to abdominal wall with only one suture
**Uterine horn no longer sutured to abdominal wall
+ Fascia removed with peritoneum and muscle layers

TABLE 6

Adhesion Scoring

| Characteristic | Adhesion Score |
|---|---|
| Extent (% sidewall involvement) | |
| None | 0 |
| ≦25 | 1 |
| ≦50 | 2 |
| ≦75 | 3 |
| >75 | 4 |
| Type | |
| None | 0 |
| Filmy, no vessels (transparent) | 1 |
| Opaque, no vessels (translucent) | 2 |
| Opaque, small vessels present grossly | 3 |
| Opaque, larger vessels present grossly | 4 |
| Tenacity | |
| None | 0 |
| Adhesions essentially fell apart | 1 |
| Adhesions lysed with traction | 2 |
| Adhesions required sharp dissection for lysis | 3 |

We claim:

1. An adhesive composition consisting essentially of
i) a first aqueous mixture of about 20–60 wt/vol % serum albumin in about 0.01–0.25 molar buffer at a pH in a range of about 8.0–11.0,
ii) a second aqueous mixture of about 50–800 mg/ml of a crosslinking agent having a molecular weight in a range of about 1,000–15,000, wherein the crosslinking agent is of the formula

G—LM—PEG—LM—G wherein —PEG— is a diradical fragment represented by the formula

—O—(CH$_2$—CH$_2$—O—)$_a$— where a is an integer from 20–300;
wherein —LM— is a diradical fragment selected from the group consisting of a carbonate diradical of the formula, —C(O)—, a monoester diradical of the formula, —(CH$_2$)$_b$C(O)— where b is an integer from 1–5, a diester diradical of the formula, —C(O)—(CH$_2$)$_c$—C(O)— where c is an integer from 2–10 and where the aliphatic portion of the diradical may be saturated or unsaturated, a dicarbonate diradical of the formula —C(O)—O—(CH$_2$)$_d$—O—C(O)— where d is an integer from 2–10, and an oligomeric diradical represented by the formulas —R—C(O)—, —R—C(O)—(CH$_2$)$_c$—C(O)—, or —R—C(O)—O—(CH$_2$)$_d$—O—C(O)— where c is an integer from 2–10, d is an integer from 2–10, and R is a polymer or copolymer having 1–10 monomeric fragments selected from the group consisting of lactide, glycolide, trimethylene carbonate, caprolactone and p-dioxanone; and wherein —G is a leaving group selected from the group consisting of succinimidyl, maleimidyl, phthalimidyl, imidazolyl, nitrophenyl or tresyl, and wherein a combination of the first and second mixtures is initially liquid and then cures on the surface of tissue to give a flexible, substantive matrix which bonds to the tissue and has a burst strength greater than about 10 mmHg.

2. The adhesive mixture of claim 1 wherein the protein in the first mixture is about 35–45 wt/vol % serum albumin.

3. The adhesive composition of claim 1 wherein the serum albumin is human serum albumin.

4. The adhesive composition of claim 1 wherein the buffer is 0.05–0.15 molar carbonate/bicarbonate buffer at a pH of about 9.0–10.5.

5. The adhesive composition of claim 1 wherein the second aqueous mixture is about 50–300 mg/ml of a crosslinking agent having a molecular weight in a range of about 1,000–5,000.

6. The adhesive composition of claim 1 wherein the ratio of a volume of the first mixture to a volume of the second mixture is in a range of about 1:10 to about 10:1.

7. The adhesive composition of claim 1 wherein —LM— is an oligomeric diradical —R—C(O)—(CH$_2$)$_c$—C(O)— where c is an integer from 2–10 and R is a polymer or copolymer having 1–10 monomeric fragments selected from the group consisting of lactide, glycolide, trimethylene carbonate, caprolactone and p-dioxanone.

8. The adhesive composition of claim 1 wherein —G is succinimidyl.

9. An in vivo method of adhering tissue comprising the steps of topically applying and bonding an adhesive mixture of claim 1 to the tissue.

10. An in vivo method of sealing air leaks in pulmonary tissues comprising the step of topically applying and curing the adhesive mixture of claims 1 to an air leak site in the pulmonary tissue.

11. An in vivo method to prevent post-surgical adhesions comprising the step of topically applying and curing the adhesive mixture of claims 1 to tissue surrounding a surgical site.

12. An in vivo method to seal tissue comprising the step of topically applying and bonding the adhesive mixture of claims 1 to tissue to prevent or control blood or other fluid leaks.

13. The adhesive composition of claim 1 wherein the second aqueous mixture is about 300–800 mg/ml of a crosslinking agent having a molecular weight in a range of about 5,000–15,000.

14. The adhesive composition of claim 13 wherein —LM— is a diester diradical of the formula —C(O)—$(CH_2)_2$—C(O)—.

15. The adhesive mixture of claim 1 wherein —LM— is a diester diradical of the formula, —C(O)—$(CH_2)_c$—C(O)— where c is an integer from 2–10 and where the aliphatic portion of the diradical may be saturated or unsaturated.

16. The adhesive composition of claim 15 wherein —LM— is a oligomeric diradical derived from polyglycolic acid.

17. A method of making a tissue adhesive consisting of the step of forming a mixture of i) a first aqueous mixture of about 20–60 wt/vol % serum albumin in about 0.01–0.25 molar buffer at a pH in a range of about 8.0–11.0, ii) a second aqueous mixture of about 50–800 mg/ml of a crosslinking agent having a molecular weight in a range of about 1,000–15,000, wherein the crosslinking agent is of the formula

G—LM—PEG—LM—G wherein —PEG— is a diradical fragment represented by the formula

—O—$(CH_2—CH_2—O—)_a$— where a is an integer from 20–300;

wherein —LM— is a diradical fragment selected from the group consisting of a carbonate diradical of the formula, —C(O)—, a monoester diradical of the formula, —$(CH_2)_b$C(O)— where b is an integer from 1–5, a diester diradical of the formula, —C(O)—$(CH_2)_c$—C(O)— where c is an integer from 2–10 and where the aliphatic portion of the diradical may be saturated or unsaturated, a dicarbonate diradical of the formula —C(O)—O—$(CH_2)_d$—O—C(O)— where d is an integer from 2–10, and an oligomeric diradical represented by the formulas —R—C(O)—, —R—C(O)—$(CH_2)_c$—C(O)—, or —R—C(O)—O—$(CH_2)_d$—O—C(O)— where c is an integer from 2–10, d is an integer from 2–10, and R is a polymer or copolymer having 1–10 monomeric fragments selected from the group consisting of lactide, glycolide, trimethylene carbonate, caprolactone and p-dioxanone; and wherein —G is a leaving group selected from the group consisting of succinimidyl, maleimidyl, phthalimidyl, imidazolyl, nitrophenyl or tresyl, and wherein a combination of the first and second mixtures is initially liquid and then cures on the surface of tissue to give a flexible, substantive matrix which bonds to the tissue and has a burst strength greater than about 10 mmHg.

* * * * *